United States Patent [19]

Rheinberger et al.

[11] Patent Number: 5,703,249

[45] Date of Patent: Dec. 30, 1997

[54] BICYCLOALIPHATIC 2-METHYLENE-1,3-DIOXEPANES

[75] Inventors: Volker Rheinberger, Vaduz; Norbert Moszner, Eschen, both of Liechtenstein; Ulrich Salz; Thomas Voelkel, both of Lindau, Germany

[73] Assignee: Ivoclar AG, Liechtenstein

[21] Appl. No.: 548,104

[22] Filed: Oct. 25, 1995

[30] Foreign Application Priority Data

Oct. 26, 1994 [DE] Germany ................ P4439485.3

[51] Int. Cl.$^6$ .................. C07D 317/44; C07D 317/72
[52] U.S. Cl. .................. 549/337; 549/338; 549/351; 526/266; 526/273; 106/35
[58] Field of Search .................. 549/337, 338, 549/351; 526/266, 273

[56] References Cited

FOREIGN PATENT DOCUMENTS

| | | |
|---|---|---|
| 206 074 | 12/1986 | European Pat. Off. . |
| 209 700 | 1/1987 | European Pat. Off. . |
| 61-069704 | 4/1986 | Japan . |
| 61-069706 | 4/1986 | Japan . |
| 2 107 341 A | 4/1983 | United Kingdom . |

OTHER PUBLICATIONS

Bailey, W.J., et al., "Free Radical Ring–Opening Polymerization of 4,7-Dimethyl-2-methylene-1,3-dioxepane and 5,6-Benzo-2-methylene-1,3-dioxepane," *Macromolecules*, 15:711–14 (1982).

Schulze, T., et al., "Crosslinking Copolymerization of Cyclic Ketenacetals With Low Shrinkage in Volume," *Macromolecular Chemistry and Physics*, 196:567–72 (1995).

Bailey, W.J., et al., "Synthesis of Poly–e–Caprolactone via a Free Radical Mechanism. Free Radical Ring–Opening Polymerization of 2-Methylene-1,3-Dioxepane," *Journal of Polymer Science*, 20:3021–30 (1982).

Endo, T., et al., "Photoinitiated Ring–Opening Polymerization of 2-Methylene-1,3-Dioxepane," *Journal of Polymer Science* 21:373–80 (1983).

Bailey, W.J., et al., "Synthesis of Functionally–Terminated Oligomers by Free Radical Ring–Opening Polymerization," *J. Macromol. Sci.–Chem.*, A21(8&9):979–95 (1984).

*Primary Examiner*—Bernard Dentz
*Attorney, Agent, or Firm*—Nixon, Hargrave, DeVans & Doyle

[57] ABSTRACT

The present invention relates to novel bicycloaliphatic 2-methylene-1,3-dioxepanes, which are suitable as starting materials for the preparation of polymers and copolymers, preferably of composite and dental materials. The 2-methylene-1,3-dioxepanes according to the invention, which can undergo radical polymerisation with ring opening with only very little volume shrinkage, can be prepared in a simple manner, are easy to purify and to modify chemically, and are characterised by lack of odour and advantageous physical properties.

17 Claims, No Drawings

BICYCLOALIPHATIC 2-METHYLENE-1,3-DIOXEPANES

The present invention relates to novel bicycloaliphatic 2-methylene-1,3-dioxepanes which can undergo radical or cationic ring-opening polymerisation with only very little volume shrinkage. The invention also relates to the use of said dioxepanes for the preparation of composite and dental materials.

It is known in the prior art that volume shrinkage of varying degrees is usually observed during the polymerisation of monomers or monomer mixtures (R. M. Luck, R. K. Sadhir, Expanding Monomers—Synthesis, Characterization and Applications; CRS Press (1992) 4). The volume shrinkage ($V_{sh}$) is defined by the formula $$V_{sh}=(V_m-V_p)/V_m$$

where $V_m$ stands for the monomer volume and $V_p$ stands for the polymer volume.

In the case of moulded bodies, said volume shrinkage is extremely prejudicial for the dimensional stability and the mechanical properties of the moulded bodies, whilst in the case of adhesive systems and bonding compounds, the adhesion properties and the bond strength are adversely affected.

A number of monomer systems are known, such as, for example, epoxy resins (B. Ellis; Chemistry and Technology of Epoxy Resins, Blackie Acad.& Profess., London 1992) or double ring-opening monomers based on spiroorthoesters and spiroorthocarbonates (R. F. Brady; J. Macromol. Sci.-Rev. Macromol. Chem. Phys. C32 (1992) 135), which polymerise with little or no volume contraction. The disadvantage of said monomer systems, however, is that photocuring at room temperature, as in the case of epoxy resins, for example, takes place only very slowly which is a disadvantage for the rapid processability of said materials. Moreover, said monomer systems and the polymers formed from them cannot be used in the medical and dental sector for toxicological reasons. Moreover, the synthesis of spiroorthoesters and spiroorthocarbonates is extremely expensive and the ring opening tendency of said compounds during radical photoinitiation is only very slight, with the result that said materials can be used only on a very limited basis and are suitable solely for special applications in which the disadvantages with regard to processability and toxicological properties are of no consequence, and the fact that the polymers are more expensive to produce is accepted in view of the properties desired for the special case.

2-Methylene-1,3-dioxepane derivatives are known in the prior art as relatively easily obtainable monomer systems which can undergo radical ring-opening polymerisation. For example, the unsubstituted 2-methylene-1,3-dioxepane is obtainable in high yields by a two-step synthesis starting from chloroacetaldehyde dimethylacetal and butane-1,4-diol (E. Taskinert, M.-L. Pentikainen, Tetrahedron 34 (1978) 2365) (cf FIG. 1).

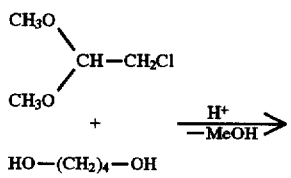

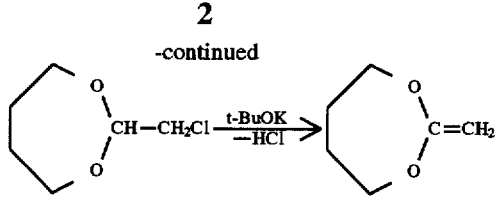

FIG. 1: Preparation of 2-methylene-1,3-dioxepane

Bailey et al. described for the first time the thermally initiated radical ring-opening polymerisadon of 2-methylene-1,3-dioxepane (W. J. Bailey et al., J. Polym. Sci., Polym. Chem. Ed. 20 (1982) 3021; W. J. Bailey et al., Proc. IUPAC Macromol. Syrup. 281h (1982) 214; Chem. Abstr. 99 (1983) 158955u), wherein it could be shown with the aid of $^{13}$C-NMR and IR spectroscopy that polymerisation takes place completely with ring opening (FIG. 2). The homopolymer formed starting from 2-methylene-1,3-dioxepane has a rubbery and waxy character.

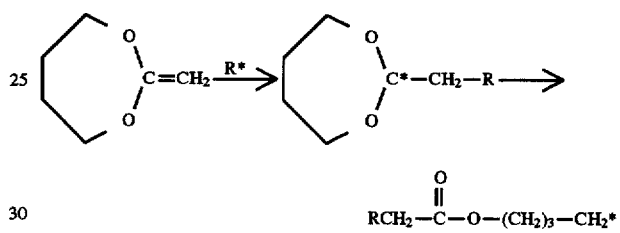

FIG. 2: Ring opening of 2-methylene-1,3-dioxepane

At room temperature (25° C.), 2-methylene-1,3-dioxepane can also be polymerised with complete ring opening by photoinitiation in the presence of 2-ethylanthraquinone or benzoin isopropylester as photoinitiator (T. Endo, M. Okawara, W. J. Bailey; J. Polym. Sci., Polym. Lett. Ed. 21 (1983) 373).

For the further investigation of the ring-opening tendency of 2-methylene-1,3-dioxepanes, Bailey et al. also prepared 5,6-benzo-2-methylene-1,3-dioxepane and a cis-trans isomer mixture of 4,7-dimethyl-2-methylene-1,3-dioxepane (Bailey et al., Macromolecules 15 (1982) 711) (of FIG. 3). Drastic reaction conditions (120° C., 15 hours in the presence of 2.5 mol % of di-t-butylperoxide (DTBP)) were required to form a solid polymer from the compound 5,6-benzo-2-methylene-1,3-dioxepane; under comparable conditions, the use of the compound 4,7-dimethyl-2-methylene-1,3-dioxepane (120° C., 72 hours, 2 mol % of DTBP) yielded only a viscous polymer, even after a prolonged reaction time. In both cases, 100% ring opening could be verified by spectroscopy.

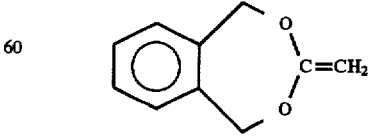

5,6-benzo-2-methylene-1,3-dioxepane

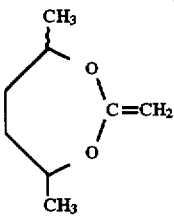

4,7-dimethyl-2-methylene-1,3-dioxepane

FIG. 3:

The copolymerisation of 2-methylene-1,3-dioxepane derivatives is also known in the prior art. For example, the compounds (2) and (3) were reacted with monomers containing vinyl groups, such as, for example, styrene and methylmethacrylate (W. J. Bailey et al., J. Macromol. Sci.-Chem. A21 (1984)979).

The use of crystalline 5,6-benzo-2-methylene-1,3-dioxepane, which is very expensive to produce, as a low-shrinkage, dentine adhesion-promoting monomer component of a dental material is described in JP 84-192346. The polymerisation shrinkage is not given for the dental materials prepared therefrom, and the dentine adhesion values of max. 5.3 MPa are extremely poor compared with other systems known in the prior art (D. H. Retief, R. S. Russell; Am. J. Dent. 7 (1994) 43).

As yet, no compounds or systems are known in the prior art which undergo only extremely little volume shrinkage during polymerisation and which, in view of their non-toxic nature and their general physical properties, are suitable in a particularly preferred manner for the preparation of composite and dental materials.

The object of the present invention is, therefore, to provide novel 2-methylene-1,3-dioxepanes as starting materials for the preparation of polymers and copolymers, preferably of dental materials, which can be prepared in a simple manner, can be cured within a short period at room temperature, polymerise with only extremely little volume shrinkage, and which have good physical properties as dental materials.

The object according to the invention is achieved by the bicycloaliphatic 2-methylene-1,3-dioxepanes according to claims 1 to 8.

According to the present invention, bicycloaliphatic 2-methylene-1,3-dioxepanes having the general formula

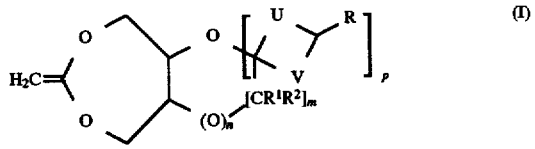

are provided, wherein n and p each equal 0 or 1 m is 0 or 1,

U and V each mean oxygen or $(CH_2)_q$, wherein q is an integer from 0 to 6,

R, $R^1$ and $R^2$ each stand for hydrogen, an alkyl group, an alkenyl group, an aryl group or a cycloaliphatic radical and may each contain a further substituent from the group comprising alkyl, vinyl, acryl, acryloxy, methacryl, methacryloxy, $COOR^3$, $CONR_2^3$ and $OR^3$, and wherein $R^3$ stands for an alkyl group and/or aryl group, wherein one of the radicals R, $R^1$ or $R^2$ may be linked to a second 2-methylene-1,3-dioxepane ring having the formula (I), or $R^1$ and $R^2$ stands for a methylene group.

The bicycloaliphatic ring system of the 2-methylene-1,3-dioxepanes according to the invention linked directly to the methylene group represents the structural unit that is responsible for ring-opening polymerisation. The other structural units which am linked to the ring which does not bear the methylene group or are which are contained therein, i.e. the spiro substituent or the group $(CR^1R^2)_m$, essentially determine the physical properties of the dioxepanes or of the polymers and copolymers prepared therefrom.

In connection with the bicycloaliphatic 2-methylene-1,3-dioxepanes, alkyl and alkylene preferably mean those groups that contain 1 to 10, preferably 1 to 6 and particularly preferably 1 to 4 carbon atom, wherein said groups may be both linear and branched. Aryl means radicals having in particular 6 to 14 carbon atoms and which may be substituted as stated above. The radicals R, $R^1$, $R^2$ and $R^3$ may each be the same or different. According to one embodiment of the invention, R, $R^1$, $R^2$ and/or $R^3$ may stand for cycloaliphatic radicals which contain up to 12 carbon atoms and may optionally be linked via bridge substituents such as, for example, $—(CH_2)_m-CO_2-$, with the 2-methylene-1,3-dioxepane framework.

According to a preferred embodiment of the invention, a bicycloaliphatic 2-methylene-1,3-dioxepane having the formula (T) is provided, in which n equals 1 and p equals 0 and wherein m, q, R, $R^1$, $R^2$ and $R^3$ have the meaning given above. Said class of dioxepanes may be represented by the general formula (II)

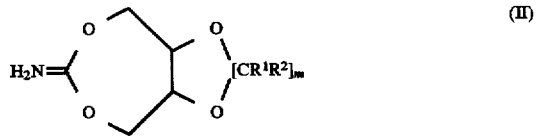

For the bicycloaliphatic dioxepanes according to the general formula (II) the radicals $R^1$ and $R^2$ are chosen preferably from the group comprising hydrogen, methyl, ethyl, cyclohexyl, norborn-1-en-5-yl and phenyl, wherein $R^1$ and $R^2$ may each be the same or different and may bear a further substituent R which has the meaning given above. In a particularly preferred manner, the substituents $R^1$ and $R^2$ stand for a methylene group.

Typical representatives of bicycloaliphatic dioxepanes having the general formula (II) are shown in Table 1.

TABLE 1

| Bicycloaliphatic 2-methylene-1,3-dioxepanes having the general formula (II) | |
|---|---|
| 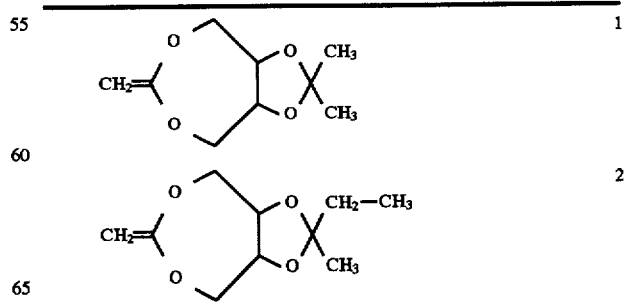 | 1 |
| | 2 |

TABLE 1-continued

Bicycloaliphatic 2-methylene-1,3-dioxepanes having the general formula (II)

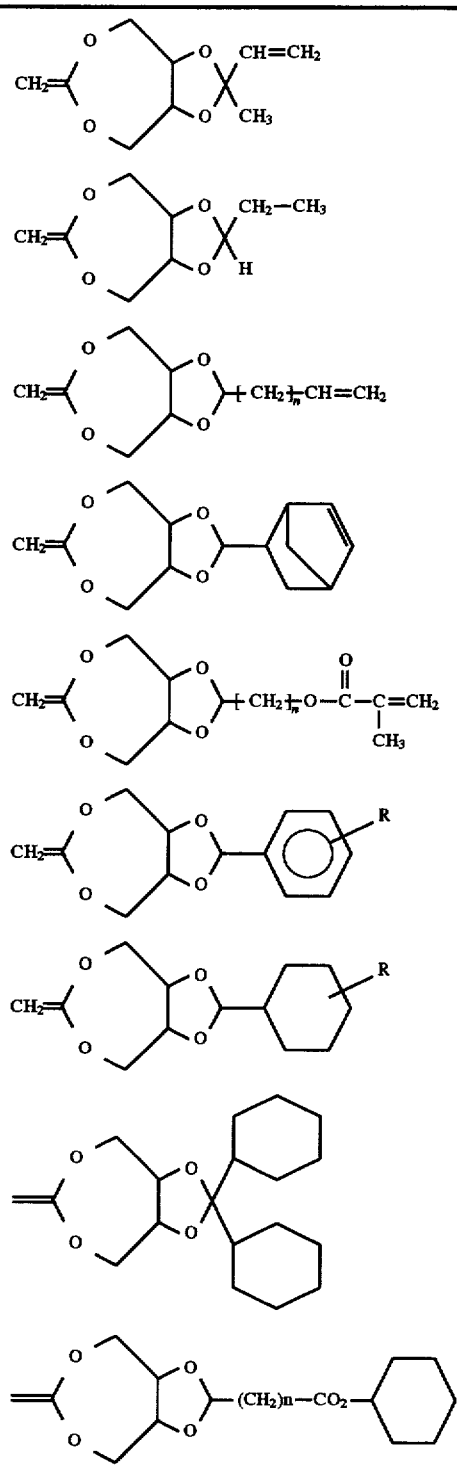

TABLE 1-continued

Bicycloaliphatic 2-methylene-1,3-dioxepanes having the general formula (II)

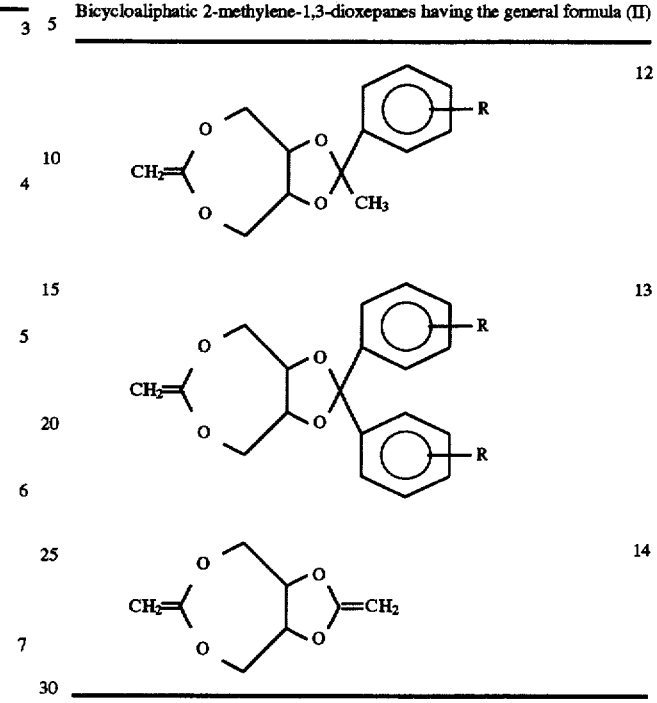

Moreover, exclusively oxygen-containing bicycloaliphatic 2-methylene-1,3-dioxepanes having the general formula (II) are preferred, in which $R^1$ means hydrogen, alkyl or aryl, and $R^2$ stands for a substituent having the formula $(CH_2)_rR$, wherein r is an integer from 0 to 4 and R is chosen from the group comprising vinyl, acryloxy and methacryloxy. Such compounds containing further polymerisable olefin groups via the ring-opening dioxepanes are of particular advantage for the preparation of polymer materials with improved mechanical properties but which do not undergo volume shrinkage during polymerisation. In a particularly preferred manner, the bicycloaliphatic dioxepanes having the general formula (II), in which m equals 1, may be linked via a phenyl radical ($R^2$) with another 2-methylene-1,3-dioxepane group having the general formula (II). In this case, the radical $R^1$ is chosen from the group comprising hydrogen, alkyl or aryl. Typical representatives of said group of dioxepanes are shown in Table. 2. These can undergo both radical and cationic cross-linking with reduced polymerisation shrinkage. According to the present invention, moreover, a dioxepane containing epoxy groups can be provided which likewise undergoes no volume shrinkage. The epoxy group is particularly suitable for further functionalisation and cross-linking (cf FIG. 4).

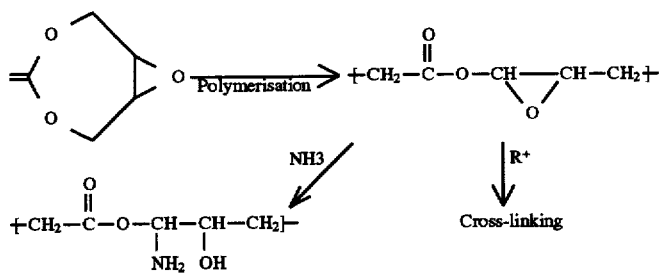

FIG. 4: Cross-linking and functionalisation via an epoxy group.

Within the context of the present invention, moreover, bicycloaliphatic dioxepanes are provided which bear on their basic framework a further ring having a spiro linkage. Said dioxepanes correspond to the general formula (III)

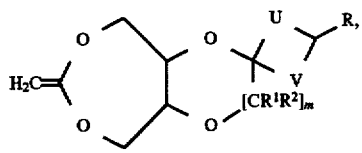

(III)

wherein m, q, U, V, R, $R^1$, $R^2$ and $R^3$ have the meaning given above.

According to a particularly preferred embodiment, bicycloaliphatic 2-methylene-1,3-dioxepane derivatives are provided which contain a cyclohexyl ring having a spiro linkage, wherein the linkage with a second 2-methylene-1, 3-dioxepane unit is also advantageous for cross-linking in the case of this group of dioxepane derivatives. Typical representatives of said dioxepanes are shown in Tables 2 and 3.

The bicycloaliphatic 2-methylene-1,3-dioxepane derivatives of the present invention are simple to obtain, for example, via the synthesis comprising four stages shown in FIG. 5. For example, trans-acetalisation of 2-bromoacetaldehyde diethylacetal with cis-2-butene-1,4-diol can take place initially in the first stage. The double bond of the dioxepane formed is subsequently oxidised to the cis-diol with potassium permanganate or an equivalent oxidising agent, and the corresponding ketal or acetal (II) is formed in the third stage by reaction with a corresponding ketone or aldehyde. After HBr dissociation, the corresponding bicycloaliphatic 2-methylene-1,3-dioxepane derivative is obtained in the fourth stage (FIG. 5).

TABLE 1

Bicycloaliphatic 2-methylene-1,3-dioxepanes having the general formula (II) and (III) with at least two 2-methylene-1,3-dioxepane units

TABLE 3

Bicycloaliphatic 2-methylene-1,3-dioxepane derivatives having the general formula (III)

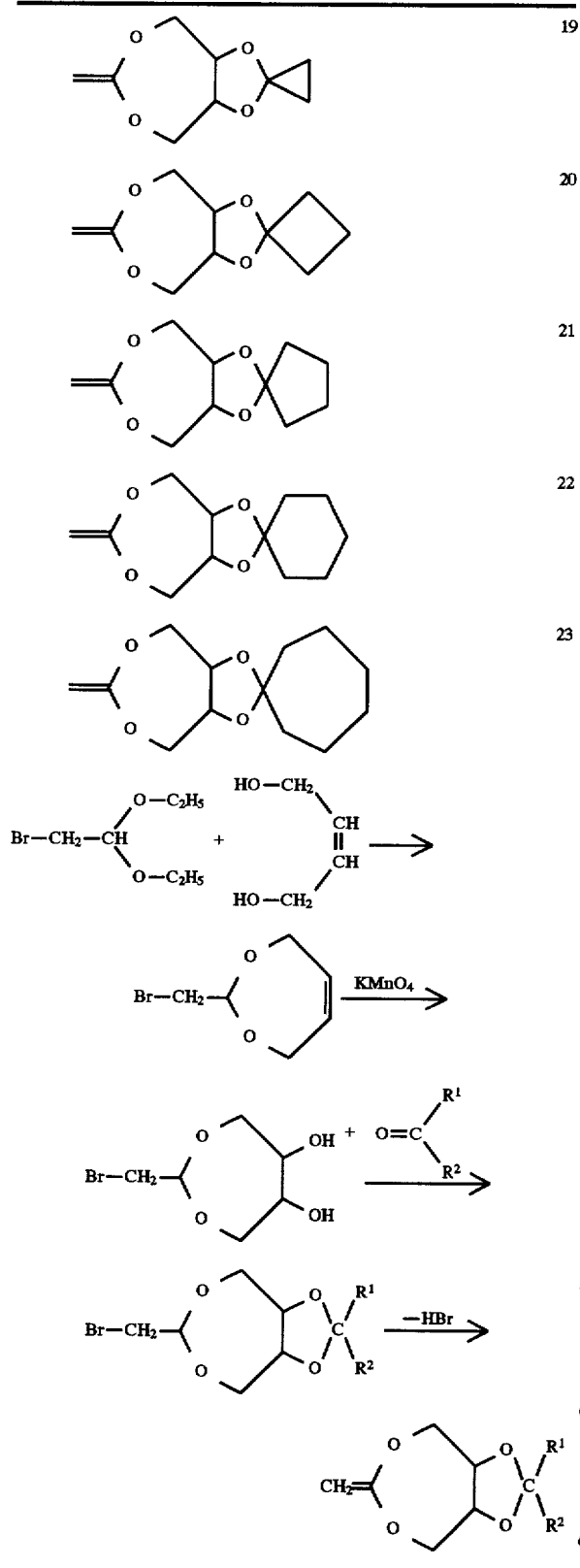

FIG. 5: Typical preparation of 2-methylene-1, 3-dioxepanes having the general formula (II)

Starting from the corresponding dialkyl acetals or dialkyl acetals, the bicycloaliphatic dioxepane derivatives having the general formula (III) can be obtained in a similar manner by trans-acetalisation (FIG. 6).

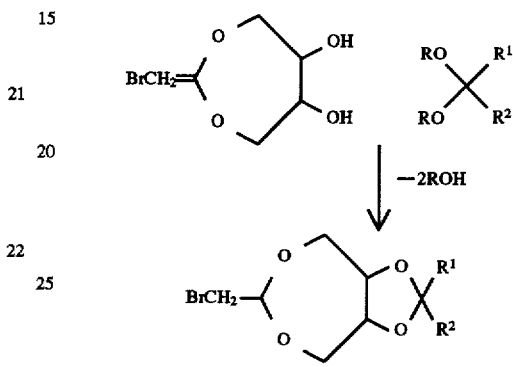

FIG. 6: Typical preparation of 2-methylene-1, 3-dioxepanes having the general formula (III)

Surprisingly, it has become apparent that the bicycloaliphatic 2-methylene-1,3-dioxepanes of the present invention have a markedly lower volume shrinkage during polymerisation than do unsubstituted 2-methylene-1,3-dioxepanes of the prior art. The compounds according to the invention are used as starting materials for the preparation of polymers and/or copolymers such as, for example, dental materials. They can be prepared in a simple manner, and can be polymerised at room temperature by radicals or cations in the presence of suitable photoinitiators, thermally, or in the presence of radical initiators or cationic initiators. Extremely little volume shrinkage occurs during said process.

For example, thermally initiated bulk homopolymerisation of 4-methylene-9,9-dimethyl-3,5,8,10-tetraoxabicyclo [5.3.0]decane with 2.5 mol % of DTP (120° C., 16 hours) takes place with a volume contraction of only 2.1%. Compared with the polymerisation of unsubstituted 2-methylene-1,3-dioxepane described by Bailey et al., the volume shrinkage of the corresponding dioxepane derivative of the present invention is thus a factor of about 3 lower than for dioxepanes of the prior art. It could be verified with the aid of $^{13}$C-NMR spectroscopy that homopolymerisation of the 4-methylene-9,9-dimethyl-3,5,8,10-tetraoxabicyclo[5.3.0] decane according to the invention takes place with complete ring opening. The polymers prepared from the bicyclic 2-methylene- 1,3-dioxepanes 4-methylene-9-ethyl-9-methyl-3,5,8, 10-tetraoxabicyclo[5.3.0]decane, 4-methylene-9-methyl-9-vinyl-3,5,8,10-tetraoxabicyclo [5.3.0]decane and 4-methylene-9-ethyl-3,5,8,10-tetraoxabicyclo[5.3.0]decane also exhibit similarly low volume shrinkage (cf Table 4).

TABLE 4

Shrinkage values for polymers obtained from bicyclic 2-methylene-1,3-dioxepanes according to the invention after photopolymerisation (cf Example 8)

| Monomers (Reference to example) | Shrinkage value (%) |
|---|---|
| Methylene-9,9-dimethyl-3,5,8,10-tetraoxabicyclo[5.3.0]decane (1) (cf Example 1) | 6.2 |
| 4-Methylene-9-ethyl-9-methyl-3,5,8,10-tetraoxabicyclo[5.3.0]decane (2) (cf Example 2) | 7.5 |
| 4-Methylene-9-methyl-9-vinyl-3,5,8,10-tetraoxabicyclo[5.3.0]decane (3) (cf Example 3) | 6.2 |
| 4-Methylene-9-ethyl-3,5,8,10-tetraoxabicyclo[5.3.0]decane (4) (cf Example 4) | 4.8 |
| Comparison: Triethyleneglycol dimethacrylate | 14.2 |
| Comparison: Decane-1,10-diol dimethacrylate | 10.1 |

According to the present invention, moreover, it can be shown that even with the copolymerisation of 2-methylene-1,3-dioxepane derivatives such as, for example, with dimethacrylates (e.g. propoxylated bis-GMA), significantly reduced polymerisation shrinkage takes place in comparison with pure dimethacrylate mixtures (cf Table 5). The bicycloaliphatic 2-methylene-1,3-dioxepanes having the general formula (I) are particularly suitable for the preparation of dimensionally stable moulded bodies and in particular for use in or as dental materials. Apart from the relatively low volume shrinkage, the polymers and copolymers prepared from the 2-methylene-1,3-dioxepanes according to the invention are characterised by being simple to prepare, simple to purify and easy to modify. The properties of the polymers can thus be specifically controlled in a simple manner by the choice of the substituents R, $R^1$, $R^2$ and/or $R^3$ in the monomer and by additional cross-linking. In particular, it has become apparent that the dioxepane derivatives of the present invention can be polymerised at room temperature in a relatively short time, wherein the preparation of the polymers can take place by irradiation in the UV or in the visible range.

The bicycloaliphatic dioxepanes of the present invention are particularly suitable for the preparation of low-shrinkage composite materials and dental materials. In particular, the 2-methylene-1,3-dioxepanes of the present invention are preferably suitable as filler material and dental adhesive. Advantageously, in addition, fillers, monomers as cross-linking agents, and/or catalysts are used, the preferred fillers being pyrogenic or precipitated silicas, amorphous silicates or metal oxides and X-ray opaque materials, such as X-ray opaque glasses, barium sulphate or ytterbium fluoride, and the preferred catalysts being dibenzoyl peroxide, dilauryl peroxide, butyl peroctate, azobisisobutyronitrile, benzpinacol (for hot polymerisation), benzyl and lauryl peroxide together with amines (for cold polymerisation). Moreover, benzophenone, benzoquinone and derivatives thereof, α-diketones, camphor quinone (for radical polymerisation), triphenyliodonium-, triphenylsulphonium salts, ferrocene derivatives (for cationic photopolymerisation) and Broenstedt and Lewis acids and combinations of the two (for cationic polymerisation), inter alia, are suitable. The additional monomers are chosen preferably from the group comprising mono- or di(meth)acrylates (such as, for example, methylmethacrylate, triethyleneglycol dimethacrylate, hexanediol dimethacrylate, dodecanediol dimethacrylate, bisphenol-A dimethacrylate, bisphenol-A glycidyl methacrylate, trimethyloylpropane trimethacrylate, urethanedimethacrylates), epoxides or vinyl ether compounds.

The bicycloaliphatic 2-methylene-1,3-dioxepanes according to the invention thus provide starting materials for the preparation of polymers and copolymers, preferably dental materials, which can be prepared in a simple manner, are virtually odourless, can be distilled and easily modified, and can undergo both radical and cationic photopolymerisation at room temperature, and can be cured thermally with and without a radical initiator, and cationically.

The present invention will be described below on the basis of examples.

Examples for the preparation and use of bicycloaliphatic 2-methylene-1,3-dioxepanes

EXAMPLE 1

4-Methylene-9,9-dimethyl-3,5,8, 10-tetraoxabicyclo[5.3.0] decane (1)

First stage: 2-Bromomethyl-4,7-dihydro-1,3-dioxepin:

A mixture of 3.22 mol (635 g) of 2-bromoacetaldehyde diethylacetal, 3.16 mol (278 g) of cis-2-butene-1,4-diol and 6 g of p-toluenesulphonic acid (catalyst) was charged to a 2 l distillation flask and stirred for 10 minutes at room temperature. The product and ethanol were then distilled under a filter pump vacuum at a bath temperature of approx. 200° C. The colourless, clear distillate then underwent fractional distillation under a filter pump vacuum, 2-bromomethyl-4,7-dihydro-1,3-dioxepin going over at 108° to 110° C. (17 mm Hg) and 523.3 g of colourless, clear product being obtained 86% yield).

$C_6H_9O_2Br$ (193.04 g/mol): Found: C 37.09, H 4.77, Br 41.59 Calculated: C 37.33, H 4.70, Br 41.39

$^1$H-NMR (CDCl$_3$, ppm): 3.42 (d, 2H, Br-CH$_2$-), 4.00–4.60 (m,4H; -CH$_2$-O-), 4.98 (t, 1H, >CH-) and 5.62–577 (m,2H, =CH-).

$^{13}$C-NMR (CDCl$_3$, ppm): 31.4 (C2), 65.8 (C3), 102.2 (C1) and 129.2 (C4).

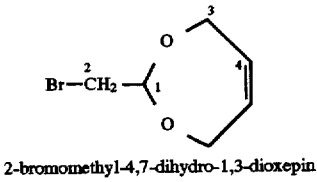

2-bromomethyl-4,7-dihydro-1,3-dioxepin

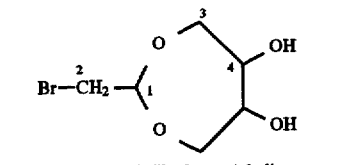

2-bromomethyl-5,6-dihydroxy-1,3-dioxepane

Second stage: 2-bromomethyl-5,6-dihydroxy-1,3-dioxepane:

907 mmol (175 g) of 2-bromomethyl-4,7-dihydro-1,3-dioxepin dissolved in 4.9 l of ethanol were cooled to −60° C. A solution of 862 mmol of potassium permanganate (136.2 g) in 1.6 l of water were added dropwise over a period of 1.5 h such that the internal temperature did not rise above −40° C. The mixture was left to stand overnight at room temperature, the manganese dioxide was filtered and the clear solution concentrated in a rotary evaporator (filter pump) until turbidity commenced. A whim crystalline substance precipitated out of the remaining solution in the refrigerator, which was recrystallised from methylene chloride. After drying under a filter pump vacuum, 194 g of 2-bromomethyl-5,6-dihydroxy-1,3-dioxepane (32% yield) were obtained, the melting range being 85° to 95° C. (determined by DSC).

$C_6H_{11}O_4Br$ (227.05 g/mol): Found: C 31.63, H 4.81, Br 35.34 Calculated: C 31.74, H 4.88, Br 35.19

$^1$H-NMR (CDCl$_3$, ppm): 2.95 (s,2H,-OH), 3.30 (d,2H,-CH$_2$Br), 3.50–4.07 (m,6H, -CH$_2$ -O- >CH-OH) and 4.95 (t, 1H,-O-C(CH$_2$Br)H-O-).

$^{13}$C-NMR (CDCl$_3$, ppm): 33.4 (C2), 66.3 (C3), 71.2 (C4) and 100.1 (C1).

Third stage: 4-bromomethyl-9,9-dimethyl-3,5,8,10-tetraoxabicyclo[5.3.0]decane:

A mixture of 0.93 mol (211 g) of 2-bromomethyl-5,6-dihydroxy-1,3-dioxepane, 5.75 mol (422 ml) of acetone, 1.8 g of p-toluenesulphonic acid and 750 ml of methylene chloride was heated under reflux and the water formed was separated by means of a water separator. After about 9 h, the methylene chloride was drawn off in the rotary evaporator (filter pump), and the residue underwent fractional distillation under a medium high vacuum. At 89°–92° C. (0.5 mbar), 231 g of 4-bromomethyl-9,9-dimethyl-3,5,8,10-tetraoxabicyclo[5,3,0]decane (93% yield) were obtained as a colourless liquid which exhibited crystalline deposits in some cases at room temperature and was a mixture of isomers.

$C_9H_{15}O_4Br$ (267.12 g/mol): Found: C 40.50, H 5.58, Br 29.70 Calculated: C 40.47, H 5.66, Br 29.91

$^1$H-NMR (CDCl$_3$, ppm): 1.25–1.65 (m,6H,-CH$_3$), 3.33–3.40 (m,2H,-CH$_2$Br), 3.66–4.45 (m,6H, -CH$_2$-O-, >CH-O-) and 5.08–5.11 (m, 1H,-O-C(CH$_2$Br)H-O-).

$^{13}$C-NMR (CDlC$_3$, ppm): 24.9, 25.0, 27.2 and 27.6 (C6), 31.1 and 31.3 (C2), 66.6, 67.0 (C3), 75.8 and 76.6 (C4), 104.3 and 105.0 (C1), 108.3 and 110.1 (C5).

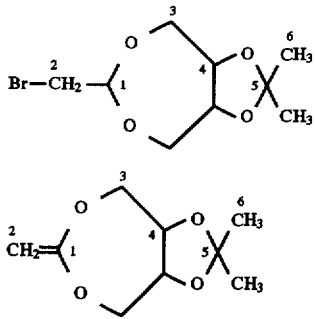

4-bromomethyl-9,9-dimethyl-3,5,8,10-tetraoxabicyclo [5.3.0]decane 1

Fourth stage: 4-methylene-9,9-dimethyl-3,5,8,10-tetraoxabicyclo[5.3.0]decane (1):

0.943 mol (105.8 g) of potassium tert.butylate were dissolved in 800 ml of water-free THF. A solution of 865 mmol (231 g) of 4-bromomethyl-9,9-dimethyl-3,5,8,10-tetraoxabicyclo[5.3.0]decane in 800 ml of THF were added dropwise within 90 minutes with stirring and the mixture was subsequently heated for 6 h under reflux. The resulting KBr was filtered and the THF was subsequently distilled under a filter pump vacuum. The dark brown residue underwent fractional distillation under vacuum. 111.2 g of colourless clear 4-methylene-9,9-dimethyl-3,5,8,10-tetraoxabicyclo[5.3.0]decane (yield 70%) go over at between 45° and 49° C. (0.2 mbar).

$C_9H_{14}O_4$ (186.21 g/mol): Found: C 57.84, H 7.55 Calculated: C 58.05, H 7.58

$^1$H-NMR (CDCl$_3$, ppm): 1.40 and 1.53 (s,6H-CH$_3$), 3.60 (s,2H, =CH$_2$), 3.72–4.30 (m, 6H, -CH$_2$-O-, >CH-O-).

$^{13}$C-NMR (CDCl$_3$, ppm): 25.7 and 28.2 (C6), 66.5 (C3), 69.6 (C2), 74.8 (C4), 109.1 (C5) and 163.1 (C1).

EXAMPLE 2

4-methylene-9-ethyl-9-methyl-3,5,8, 10-tetraoxabicyclo [5.3.0]decane (2)

First stage: 4-bromomethyl-9-ethyl-9-methyl-3,5,8, 10-tetraoxabicyclo [5.3.0]decane 4-Bromomethyl-9-ethyl-9-methyl-3,5,8,10-tetraoxabicyclo[5.3.0]decane was prepared in a similar way to 4-bromomethyl-9,9-dimethyl-3,5,8,10-tetraoxabicyclo [5.3.0]decane starting from 198.2 mmole (45 g) of 2-bromomethyl-5,6-dihydroxy-1,3-dioxepane and 1.225 mol (88.3 g) of ethylmethylketone, fractional distillation giving 46 g (82% yield) from 95° to 100° C. (0.25 mbar).

$C_{10}H_{17}O_4Br$ (281.15 g/mol): Found: C 42.66, H 5.91, Br 28.24 Calculated: C 42.72, H 6.09, Br 28.42

$^{13}$H-NMR (CDCl$_3$, ppm): 0.93 (t,3H,CH$_3$-CH$_2$-), 1.30 and 1.38 (t,3H,-CH$_3$), 1.65 (q,2H,H$_3$C-CH$_2$-), 3.30 and 3.37 (s,2H,-CH$_2$Br), 3.63–4.60 (m,6H,-CH$_2$-O-, >CH-O-) and 4.75 and 4.77 (t, 1H,-O-C(CH$_2$Br)H-O-).

$^{13}$C-NMR (CDCl$_3$, ppm): 7.9 and 8.7 (C8), 22.9 and 24.3 (C6), 31.4 and 32.8 (C2 and C7), 67.5 and 67.8 (C3), 75.5 and 76.2 (C4), 104.4 and 105.1 (C1), 110.7 and 111.8 (C5).

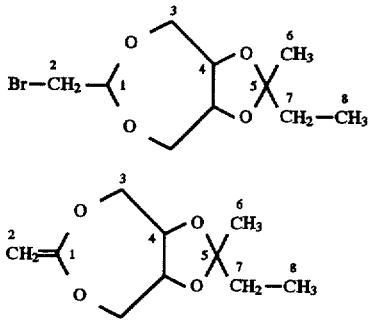

4-bromomethyl-9-ethyl-9-methyl-3,5,8,10-tetraoxabicyclo [5.3.0]decane 2

Second stage: 4-methylene-9-ethyl-9-methyl-3,5,8, 10-tetraoxabicyclo[5.3.0]decane (2):

4-Methylene-9-ethyl-9-methyl-3,5,8, 10-tetraoxabicyclo [5.3.0]decane was prepared in a similar way to 4-methylene-9,9-dimethyl-3,5,8, 10-tetraoxabicyclo [5.3.0]decane starting from 142.3 mmol (40 g) of 4-bromomethyl-9-ethyl-9-methyl-3,5,8,10-tetraoxabicyclo [5.3.0]decane, fractional distillation giving 23 g (89% yield) from 53° to 56° C. (0.2 mbar).

$C_9H_{16}O_4$ (200.23 g/mol): Found: C 59.85, H 7.93 Calculated: C 59.99, H 8.06

$^1$H-NMR (CDCl$_3$, ppm): 0.93 and 0.97 (t, 3H,CH$_3$-CH2-) 1.32 and 1.43 (t,3H, -CH), 1.65 (q,2H,H$_3$C-CH$_2$-), 3.57 (s,2H, =CH$_2$), 3.80–4.33 (m,6H,-CH$_2$-O-, >CH-O-).

$^{13}$C-NMR (CDCl$_3$, ppm): 8.5 and 8.9 (C8), 22.9 and 25.3 (C6), 31.6 and 34.0 (C7), 68.4 and 69.6 (C2 and C3), 74.2 and 74.7 (C4), 110.9 and 111.34 (C5), 163.3 and 163.7 (C1).

EXAMPLE 3

4-Methylene-9-methyl-9-vinyl-3,5,8, 10-tetraoxabicyclo [5.3.0]decane (3)

First stage: 4-bromomethyl-9-methyl-9-vinyl-3,5,8, 10-tetraoxabicyclo[5.3.0]decane 4-Bromomethyl-9-methyl-9-vinyl-3,5,8,10-tetraoxabicyclo[5.3.0]decane was prepared in a similar way to 4-bromomethyl-9,9-dimethyl-3,5,8, 10-tetraoxabicyclo [5.3.0]decane starting from 220 mmol (50 g) of 2-bromomethyl-5,6-dihydroxy-1,3-dioxepane and from 1.36 mol (95.5 g) of methylvinyl ketone, fractional distillation giving 33.2 g of 4-bromomethyl-9-methyl-9-vinyl-3,5,8, 10-tetraoxabicyclo [5.3.0]decane (54% yield) with a boiling point from 94° to 101° C. (0.2 mbar).

¹H-NMR (CDCl₃, ppm): 1.42 and 1.47 (s,3H,CH₃-), 3.32 and 3.35 (s,2H,-CH₂Br), 3.53–4.57 (m,6H,-CH₂-O-, >CH-O-), 4.80 (t, ¹H,-O-C(CH₂Br)H-O-), 5.07–5.50 (m,2H, =CH₂) and 5.80 (dd, 1H,-CH=).

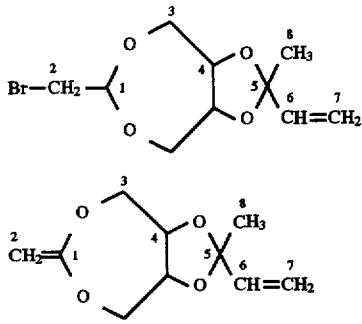

4-bromomethyl-9-methyl-9-vinyl-3,5,8, 10-tetraoxabicyclo [5.3.0]decane 3

Second stage: 4-methylene-9-methyl-9-vinyl-3,5,8, 10-tetraoxabicyclo[5.3.0]decane (3):

4-Methylene-9-methyl-9-vinyl-3,5,8,10-tetraoxabicyclo [5.3.0]decane was prepared in a similar way to 4-methylene-9,9-dimethyl-3,5,8,10-tetraoxabicyclo[5.3.0]decane starting from 115.7 mmol (35 g) of 4-bromomethyl-9-methyl-9-vinyl-3,5,8, 10-tetraoxabicyclo[5.3.0]decane, fractional distillation giving 10 g (43.2% yield) at 62° C. (0.1 mbar).

¹H-NMR (CDCl₃, ppm): 1.42 and 1.52 (s,3H,CH₃-), 3.22 and 3.58 (s,2H, =CH₂), 3.80–4.37 (m,6H,-CH₂-O-, >CH-O-), 5.03–5.58 (m,2H, =CH₂) and 5.80 (dd,1H,-CH=).

¹³C-NMR (CDCl₃, ppm): 24.7, 24.9 and 26.5 (C8), 66.1, 66.5 and 69.6 (C3), 74.6 and 74.8 (C4), 107.6 and 108.7 (C5), 114.7 and 115.3 (C7), 137.8, 138.4 and 139.8 (C6) and 163.1 and 163.6 (C1).

EXAMPLE 4

4-Methylene-9-ethyl-3,5,8, 10-tetraoxabicyclo[5.3.0]decane (4)

First stage: 4-bromomethyl-9-ethyl-3,5,8, 10-tetraoxabicyclo [5.3.0]decane

4-Bromomethyl-9-methyl-3,5,8,10-tetraoxabicyclo [5.3.0]decane was prepared in a similar way to 4-bromomethyl-9,9-dimethyl-3,5,8, 10-tetraoxabicyclo [5.3.0]decane starting from 132 mmol (30 g) of 2-bromomethyl-5,6-dihydroxy-1,3-dioxepane and from 0.816 mol (60 ml) of propionaldehyde, fractional distillation giving 25 g (71% yield) from 100° to 102° C. (0.4 mbar).

C₉H₁₅O₄Br (267.12 g/mol): Found: C 42.48, H 5.89, Br 26.95 Calculated: C 40.47, H 5.66, Br 29.91

¹H-NMR (CDCl₃, ppm): 0.83–1.13 (m,3H, CH₃-CH2-), 1.30 and 1.52–1.87 (m,2H,H₃C-CH₂-), 3.32 (s,2H,-CH₂Br), 3.57–4.43 (m,6H,-CH₂-O-, >CH-O-) and 4.70–5.00 (m,2H, -O-C(CH₂Br)H-O-, >C(C2H5)H).

¹³C-NMR (CDCl₃, ppm): 8.0 (C7), 26.9 (C6), 31.3 (C2), 67.1 (C3), 76.7 (C4), 105.4 and 106.0 (C1 and C5).

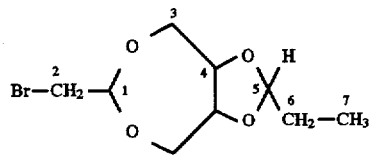

4-bromomethyl-9-ethyl-3,5,8,10-tetraoxabicyclo [5.3.0] decane 4

Second stage: 4-methylene-9-ethyl-3,5,8, 10-tetraoxabicyclo[5.3.0]decane (4):

4-Methylene-9 -ethyl-3,5,8, 10-tetraoxabicyclo [5.3.0] decane was prepared in a similar way to 4-methylene-9,9-dimethyl-3,5,8, 10-tetraoxabicyclo[5.3.0]decane starting from 131 mmol (35 g) of 4-bromomethyl-9-ethyl-3,5,8, 10-tetraoxabicyclo[5.3.0]decane, fractional distillation from 65° to 68° C. (0.3 mbar) giving 12.5 g (51% yield).

C₉H₁₄O₄ (186.06 g/mol): Found: C 57.38, E 7.48 Calculated: C 58.05, E 7.58

¹H-NMR (CDCl₃, ppm): 1.00 (t,3H,CH₃-CH₂-), 1.53–1.90 (m,2H,H₃C-CH₂-), 3.60 (s,2H, =CH₂), 3.80–4.30 (m,6H,-CH₂-O-, >CH-O-) and 4.93 (t, 1H, >C(C₂H₅)H).

EXAMPLE 5

Spiro[cyclohexane-1,1'-(6-methylene-2,5,7,10-tetraoxabicyclo[5.3.0]decane)](22)

First stage: Spiro[cyclohexane-1,1'-(6-bromomethyl-2,5,7, 10-tetraoxabicyclo[5.3.0]decane]:

The dioxane was prepared in a similar way to 4-bromomethyl-9,9-dimethyl-3,5,8,10-tetraoxabicyclo [5.3.0]decane starting from 220 mmol (50 g) of 2-bromomethyl-5,6-dihydroxy-1,3-dioxepane and from 134 g (1.36 mmol) of cyclohexanone, fractional distillation giving 32.1 g of product (47% yield) from 140° to 155° C. (0.01 mbar).

C₁₂H₁₉BrO₄ (307.14 g/mmol) Found: C 48.69, H 6.46, Br 24.87 Calculated: C 46.93, H 6.23, Br 26.05

¹H-NMR (CDCl₃); ppm; Varian 90 MHz):

1.6 (m, CH₂ cyclohexyl), 3.3 (dd, CH₂Br), 3.6–4.5 (many m, CHO and CH₂O), 4.8 (t,O-CH-O).

¹³C-NMR (CDCl₃, ppm; Bruker 300 MHz):

110.7 (C2), 105.0 (C5), 75.6 (C4), 67.2 (C3), 37.0 (C1), 34.4 (C6), 31.1 (C8), 25.2 (C7)

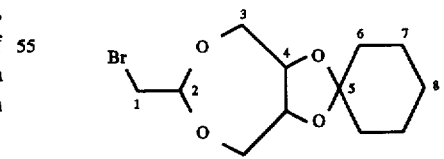

Spiro[cyclohexane-1,1'-(6-bromomethyl-2,5,7,10-tetraoxabicyclo [5.3.0]decane] 22

Second stage: Spiro[cyclohexane-1,1'-(6-methylene-2,5,7,10-tetraoxabicyclo[5.3.0]decane)](22):

The dioxepane was prepared in a similar way to 4-methylene-9,9-dimethyl-3,5,8,10-tetraoxabicyclo[5.3.0] decane starting from 115.7 mmol (35 g) of spiro [cyclohexane-1,1'-(6-bromomethyl-2,5,7,10-tetraoxabicyclo[5.3.0]decane)], fractional distillation giving 8.5 g (38.5% yield) at 98° to 104° C. (0.1 mbar).

$C_{12}H_{18}O_4$ (226.12 g/mol) Found: C 63.59, H 8.01 Calculated: C 64.74, H 8.02

$^1$H-NMR (CDCl$_3$, ppm; Varian 90 MHz): 1.7 (m, CH$_2$ cyclohexyl) 3.6 (s, =CH$_2$), 3.8–4.4 m, CHO and CH$_2$O)

$^{13}$C-NMR (CDCl$_3$; ppm; Bruker 300 MHz): 163.5 (C2), 109.7 (C5), 74.4 (C4), 69.5 (C1), 66.7 (C3), 38.1, 35.1, 27.0, 25.0, 24.1 (cyclohexyl)

EXAMPLE 6

4-Methylene-9-phenyl-3,5,8,10-tetraoxabicyclo [5.3.0](8, R=H)

First stage: 4-bromomethyl-9-phenyl-3,5,8,10-tetraoxabicyclo[5.3.0]:

4-Bromomethyl-9-phenyl-3,5,8,10-tetraoxabicyclo [5.3.0]decane was prepared in a similar way to 4-bromomethyl-9,9-dimethyl-3,5,8, 10-tetraoxabicyclo [5.3.0]decane from 64.7 g of 2-bromomethyl-5,6-dihydroxy- 1,3-dioxepane (285 mmol) and 187.0 g of benzaldehyde ( 1760 mmol) in chloroform. The reaction time was 8 days, a fresh spatula tip of toluenesulphonic acid being added every day.

Distillation in a medium high vacuum (b.p.$_{p0.1mbar}$: 130° to 169° C.) gave 69.7 g (=77.7% yield) of a neon-yellow liquid.

$^1$H-NMR (CDCl$_3$); ppm; Varian 90 MHz):
7.5 (–, aromat), 3.3 (dd, CH$_2$Br), 3.6–4.5 (many m, CHO and CH$_2$O), 4.8 (t, O-CH-O).

$^{13}$C-NMR (CDCl$_3$, ppm; Bruker 300 MHz):
31.7 (C1), 103.8 (C2), 67.2 (C3), 73.9 (C4), 104.5 (C5), 125.4, 128.4, 13.6 and 143.4 (arom. C)

IR (KBr, cm$^{-1}$): 3036, 2882, 1700, 1599

$C_{13}H_{15}BrO_4$ (315 g/mmol) Calculated: C 49.52, H 4.76, Br 25.40, O 20.32 Found: C 54.69, H 4.91, Br 18.05, O 22.35

4-bromomethyl-9-phenyl-3,5,8, 10-tetraoxabicyclo[5.3.0]8

Second stage: 4-Methylene-9-phenyl-3,5,8, 10-tetraoxabicyclo[5.3.0]decane (8):

69.6 g of 4-bromomethyl-9-phenyl-3,5,8, 10-tetraoxabicyclo [5.3.0]decane were reacted with 31.1 g of potassium-tert.-butoxide, as described in example 1 (4-methylene-9,9-dimethyl-3,5,8,10-tetraoxabicyclo[5.3.0] decane). After the usual purification stages, the product was distilled under a medium high vacuum (b.p.$_{p0.5\ mbar}$: 98° to 132° C.). After cooling, a white solid formed (m.p. 64° C.). Yield 27.1 g=44.7%.

$^1$H-NMR (CDCl$_3$), ppm; Varian 90 MHz): 3.6 (s, =CH$_2$), 3.8–4.4 (m,CHO and CH$_2$O)

$^{13}$C-NMR (CDCl$_3$); ppm; Bruker 300 MHz):
69.9 (C1), 163.1 (C2), 66.0 (C3), 75.4 (C4), 103.3 (C5), 126.6, 128.3, 128.9 and 129.6 (arom. C)

$C_{13}H_{14}O_4$ (234 g/mol) Calculated: C 66.70, H 5.97, 0 27.33 Found: C 66.79, H 6.04, O 27.17

Homopolymerisation of 4-methylene-9,9-dimethyl-3,5,8, 10-tetraoxabicyclo[5.3.0]decane (1)

EXAMPLE 7

Bulk polymerisation 1.0 g of monomer, mixed with 2.5 mmol % of AIBN, were left for 16 hours at 120° C. The white product was dissolved in THF and reprecipitated in hexane. 54.5% of precipitable product was obtained with an $M_n$ (GPC) of 7100 g/mol.

$^1$H-NMR (90 MHz, ppm): 1.19–1.30 (m): CH$_3$ terminal groups; 1.35 (s,3H) and 1.42 (s,3H): -CH$_3$; 1.70–1.98 (m,2H): >CH-CH$_2$-; 2.37–2.77 (m,2H): -CH$_2$-CO-; 3.93–4.45 (m,4H): >CH- and -CO-O-CH$_2$-.

$^{13}$C-NMR (CDCl$_3$), ppm): 14.7 (CH$_3$ terminal groups), 24.6 and 28.0 (C6), 30.8 (C8), 63.0 and 63.3 (C3), 72.5, 75.0, 75.2 and 75.7 (C4 and C7), 108.3 and 108.7 (C5) and 172.7 (C2).

IR (KBr, cm$^{-1}$): 1740 (C=O).

EXAMPLE 8

Cationic ring-opening polymerisation 0.80 wt. % of Cyacure UVI 6974 (triarylsulphonium hexafluoroantimonate, 50% in propylene carbonate) were dissolved in 4-methylene-9,9-dimethyl-3,5,8,10-tetraoxabicyclo[5.3.0]decane. A 500 μm thick film of said mixture was irradiated for 3 minutes on each side with a UV/VIS lamp (Spectramat® made by Ivoclar, wave length range 260 to above 600 nm), with the exclusion of air. The polymer obtained is sparingly soluble in e.g. hexane. The soluble proportion has the $^1$H-NMR and $^{13}$C-NMR spectra given in example 7.

EXAMPLE 9

7.80 wt. % of dioxepane from example 1 were kneaded to a homogeneous mass with 31.60% of propoxylated bisphenol-A-dimethacrylate, 41.28% of pyrogenic silica gel, 18.70 g of YbF$_3$, 0.24% of camphor quinone, 0.23% of N,N-diethyl-3,5-di-tert.-butylaniline, 0.14% of soda paste and 0.01% of butylhydroxytoluene. Said mass was irradiated in a moulded body with the exclusion of air for 3 minutes with a UV/VIS lamp (Spectramat® made by Ivoclar, wave length range 260 to over 600 nm). The measured polymerisation shrinkage was 1.9%. For comparison, a volume shrinkage of 4.2% was determined on a composite of the same composition containing decane-1,10-diol diemethacrylate instead of the dioxepane component.

We claim:

1. Bicycloaliphatic 2-methylene-1,3-dioxepanes having the general formula

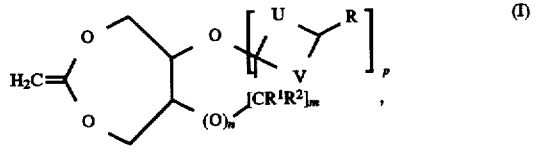

wherein n and p each equal 0 or 1, m equals 0 or 1,

U and V each mean oxygen or $(CH_2)_q$, wherein q is an integer from 0 to 3,

R, $R^1$ and $R^2$ each stand for hydrogen, an alkyl group, an alkenyl group, an aryl group or a cycloaliphatic radical and may each contain a further substituent from the group comprising alkyl, vinyl, acryl, acryloxy, methacryl, methacryloxy, $COOR^3$, $CONR_2^3$ and $OR^3$, and wherein $R^3$ stands for an alkyl group and/or aryl group, wherein one of the radicals R, $R^1$ or $R^2$ may be linked with a second 2-methylene-1,3-dioxepane ring having the formula (I), or $R^1$ and $R^2$ stands for a methylene group.

2. Dioxepane according to claim 1, characterised in that n equals 1 and p equals 0 and corresponds to the general formula

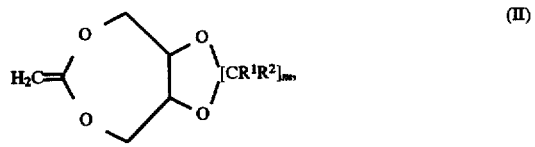

wherein m, q, R, $R^1$, $R^2$ and $R^3$ have the meaning given above.

3. Dioxepane according to claim 1, characterised in that n equals 1 and p equals 1 and corresponds to the general formula

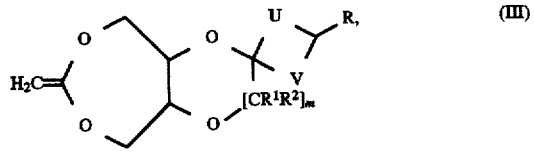

wherein m, q, U, V, R, $R^1$, $R^2$ and $R^3$ have the meaning given above.

4. Dioxepane according to claim 2, characterised in that m equals 1, and $R^1$ and $R^2$ is chosen from the group comprising hydrogen, methyl, ethyl, cyclohexyl, norborn-1-en-5-yl and phenyl, wherein $R^1$ and $R^2$ may each be the same or different and may bear another substituent R which has the meaning given above, or $R^1$ and $R^2$ stand for a methylene group.

5. Dioxepane according to claim 2, characterised in that m equals 1, $R^1$ means hydrogen and $R^2$ stands for a substituent having the formula $(CH_2)_rR$, wherein r is an integer from 0 to 4 and R is chosen from the group comprising vinyl, acryloxy and methacryloxy.

6. Dioxepane according to claim 2, characterised in that m equals 1, $R^1$ means hydrogen and $R^2$ means phenyl, wherein the phenyl group is substituted in the meta or para position by a second 2methylene-1,3-dioxepane group having the general formula (II), in which n and m are equal to 1, $R^1$ means hydrogen and $R^2$ is the linkage point to the phenyl group.

7. Dioxepane according to claim 3, characterised in that m equals 0, U and V each mean $CH_2CH_2$ and R stands for hydrogen.

8. Dioxepane according to claim 3, characterized in that m equals 0, U and V each mean $CH_2CH_2$ and R stands for a second 2-methylene-1,3-dioxepane group having the general formula

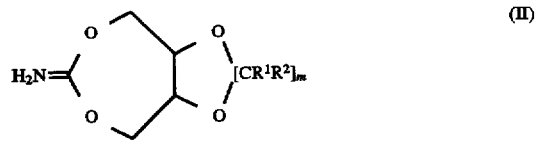

which is linked with the ring containing U and V in the form of a spiro linkage at the carbon bearing $R^1$ and $R^2$, wherein $R^1$ and $R^2$ of the second 2-methylene-1,3-dioxepane group are absent, and n and m are equal to 1.

9. A process for the preparation of polymers and/or copolymers comprising:

polymerizing the 2-methylene-1,3-dioxepane according to claim 1.

10. A process according to claim 9, wherein said polymerizing is carried out by irradiation, thermally, or with the aid of radical initiators or cationic initiators.

11. A process according to claim 9 further comprising:

forming composite materials from the polymers and/or copolymers.

12. A process according to claim 11 further comprising:

blending fillers, additional monomers as cross-linking agents, and/or catalysts with the dioxepane prior to said polymerizing.

13. A process according to claim 12, wherein the fillers are selected from the group consisting of silicates, glasses, and metal oxides.

14. A process according to claim 12, wherein the additional monomers are selected from the group consisting of acrylates, methacrylates, diacrylates, dimethacrylates, vinyl ethers, and epoxides.

15. A process according to claim 12, wherein the catalysts are selected from the group consisting of radical and cationic initiators or initiator systems, and radical and cationic photoinitiators.

16. A process according to claim 9 further comprising:

preparing dental materials from the polymers and/or copolymers.

17. A process according to claim 16, wherein the dental material is a temporary filling material or a dental adhesive.

* * * * *